(12) United States Patent
Huthmacher et al.

(10) Patent No.: US 10,646,659 B2
(45) Date of Patent: May 12, 2020

(54) MEDICAMENT DELIVERY DEVICE

(71) Applicant: Sanofi-Aventis Deutschland GMBH, Frankfurt am Main (DE)

(72) Inventors: Winfried Huthmacher, Frankfurt (DE); Peter Nober, Rommersheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 614 days.

(21) Appl. No.: 15/111,957

(22) PCT Filed: Jan. 27, 2015

(86) PCT No.: PCT/EP2015/051594
§ 371 (c)(1),
(2) Date: Jul. 15, 2016

(87) PCT Pub. No.: WO2015/113968
PCT Pub. Date: Aug. 6, 2015

(65) Prior Publication Data
US 2016/0331904 A1 Nov. 17, 2016

(30) Foreign Application Priority Data

Jan. 30, 2014 (EP) .................................. 14153202

(51) Int. Cl.
*A61M 5/315* (2006.01)
*A61M 5/32* (2006.01)
*A61M 5/31* (2006.01)

(52) U.S. Cl.
CPC ........ *A61M 5/3157* (2013.01); *A61M 5/3204* (2013.01); *A61M 5/326* (2013.01);
(Continued)

(58) Field of Classification Search
CPC ........ A61M 5/3157; A61M 2005/3143; A61M 5/31578; A61M 5/31501; A61B 18/1233
See application file for complete search history.

(56) References Cited

U.S. PATENT DOCUMENTS 4,865,591 A * 9/1989 Sams ................ A61M 5/31553
604/186
5,380,295 A * 1/1995 Vacca ................... A61M 5/315
604/187
(Continued)

FOREIGN PATENT DOCUMENTS

CA 2841172 1/2013
CN 102019012 4/2011
(Continued)

OTHER PUBLICATIONS

International Search Report and Written Opinion in International Application No. PCT/EP2015/051594, dated Jun. 3, 2015, 11 pages.
(Continued)

*Primary Examiner* — Rebecca E Eisenberg
*Assistant Examiner* — Melissa A Snyder
(74) *Attorney, Agent, or Firm* — Fish & Richardson P.C.

(57) ABSTRACT

Described is a medicament delivery device (1), comprising a body (2), a container carrier (7) for retaining a medicament container within the body (2) and being slidably disposed in the body (2), a sleeve (6) slidably coupled to body (2), and a piston rod (11) coupled to the body (2) and the container carrier (7). The piston rod (11) and the container carrier (7) provide a feedback as the container carrier (7) moves from a first position (P1) to a second position (P2) relative to the body (2).

20 Claims, 10 Drawing Sheets

Specification includes a Sequence Listing.

(52) U.S. Cl.
CPC ... *A61M 5/3287* (2013.01); *A61M 2005/3143* (2013.01); *A61M 2005/3247* (2013.01); *A61M 2005/3267* (2013.01); *A61M 2205/581* (2013.01); *A61M 2205/582* (2013.01); *A61M 2205/583* (2013.01)

(56) References Cited

U.S. PATENT DOCUMENTS

| | | | |
|---|---|---|---|
| 6,241,709 | B1 * | 6/2001 | Bechtold ............ A61M 5/2033 604/207 |
| 2008/0262438 | A1 * | 10/2008 | Bollenbach ......... A61M 5/2033 604/207 |
| 2009/0204076 | A1 | 8/2009 | Liversidge |
| 2010/0137792 | A1 | 6/2010 | Boyd et al. |
| 2011/0092915 | A1 * | 4/2011 | Olson ............... A61M 5/31501 604/198 |
| 2013/0204229 | A1 | 8/2013 | Olson et al. |

FOREIGN PATENT DOCUMENTS

| | | |
|---|---|---|
| JP | H10-504474 | 5/1998 |
| JP | H11-514242 | 12/1999 |
| JP | 2008-503296 | 2/2008 |
| JP | 2011-509783 | 3/2011 |
| JP | 2012-510326 | 5/2012 |
| JP | 2012-520128 | 9/2012 |
| JP | 2013-529520 | 7/2013 |
| JP | 2013-529990 | 7/2013 |
| WO | WO 95/32749 | 12/1995 |
| WO | WO 2006/000785 | 1/2006 |
| WO | WO 2009/092807 | 7/2009 |
| WO | WO 2010/063707 | 6/2010 |
| WO | WO2010/104779 | 9/2010 |
| WO | WO 2012/000838 | 1/2012 |
| WO | WO2012/000838 | 1/2012 |
| WO | WO 2012/000872 | 1/2012 |
| WO | WO 2012/085034 | 6/2012 |
| WO | WO 2013/007393 | 1/2013 |
| WO | WO2013/034984 | 3/2013 |
| WO | WO 2014/012994 | 1/2014 |

OTHER PUBLICATIONS

International Preliminary Report on Patentability in International Application No. PCT/EP2015/051594, dated Aug. 2, 2016, 8 pages.
Rote Liste, "50. Hypophysen-, Hypothalamushormone, andere regulatorische Peptide u. ihre Hemmstoffe," Chapter 50, ed. 2008, 20 pages.

* cited by examiner

MEDICAMENT DELIVERY DEVICE

CROSS-REFERENCE TO RELATED APPLICATIONS

This application is a U.S. national stage application under 35 USC § 371 of International Application No. PCT/EP2015/051594, filed on Jan. 27, 2015, which claims priority to European Patent Application No. 14153202.8, filed on Jan. 30, 2014, the entire contents of which are incorporated herein by reference.

TECHNICAL FIELD

The invention relates to a medicament delivery device.

BACKGROUND OF THE INVENTION

Administering an injection is a process which presents a number of risks and challenges for users and healthcare professionals, both mental and physical. Pre-filled syringes that are filled with a selected dosage of a medicament for administering the medicament to a patient are known in the art. Conventional medicament delivery devices comprising a needle safety system for preventing needle stick injuries are also known.

There remains a need for an improved medicament delivery device.

SUMMARY OF THE INVENTION

Certain aspects of the present invention relate to an improved medicament delivery device.

In an exemplary embodiment, a medicament delivery device according to the present invention comprises a body, a container carrier for retaining a medicament container within the body and being slidably disposed in the body, a sleeve slidably coupled to body, and a piston rod coupled to the body and the container carrier. The piston rod and the container carrier provide a feedback as the container carrier moves from a first position to a second position relative to the body.

In an exemplary embodiment, the piston rod is coupled to the body in a manner preventing relative movement between the piston rod and the body.

In an exemplary embodiment, the medicament delivery device further comprises a spring arranged between the body and the sleeve and biasing the sleeve in a distal direction relative to the body.

In an exemplary embodiment, the sleeve comprises a proximal stop and a distal stop adapted to abut the medicament container.

In an exemplary embodiment, the sleeve comprises one or more sleeve windows.

In an exemplary embodiment, the container carrier comprises at least one first protrusion adapted to distally abut the medicament container.

In an exemplary embodiment, the container carrier comprises one or more radially inwardly biased second legs adapted to engage a ratchet toothing on the piston rod in such a manner that the container carrier can move in the proximal direction but is prevented from moving in the distal direction relative to the piston rod.

In an exemplary embodiment, the medicament delivery device further comprises at least one clamp arranged on the container carrier and adapted to proximally abut the medicament container. The body includes a rib radially abutting the clamp to maintain the clamp in a first angular position when the container carrier is in the first position, and the clamp deflects radially to a second angular position when the container carrier is in the second position. The clamp is adapted to axially abut the sleeve in the second angular position when the container carrier is in the second position. The sleeve comprises one or more sleeve legs extending in the proximal direction adapted to radially outwardly support the clamp.

In an exemplary embodiment, the piston rod includes a deformable syringe retarder defining a diameter greater than an internal diameter of the medicament container. The deformable syringe retarder deforms on application of a predefined force on the medicament container in the proximal direction relative to the piston rod. The clamp comprises a proximal hook adapted to proximally engage the medicament container.

In an exemplary embodiment, the sleeve comprises a collar adapted to distally abut an axial stop on the body.

In an exemplary embodiment, a cap is arrangeable over a distal end of the body. The cap is adapted to engage a protective needle shield.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
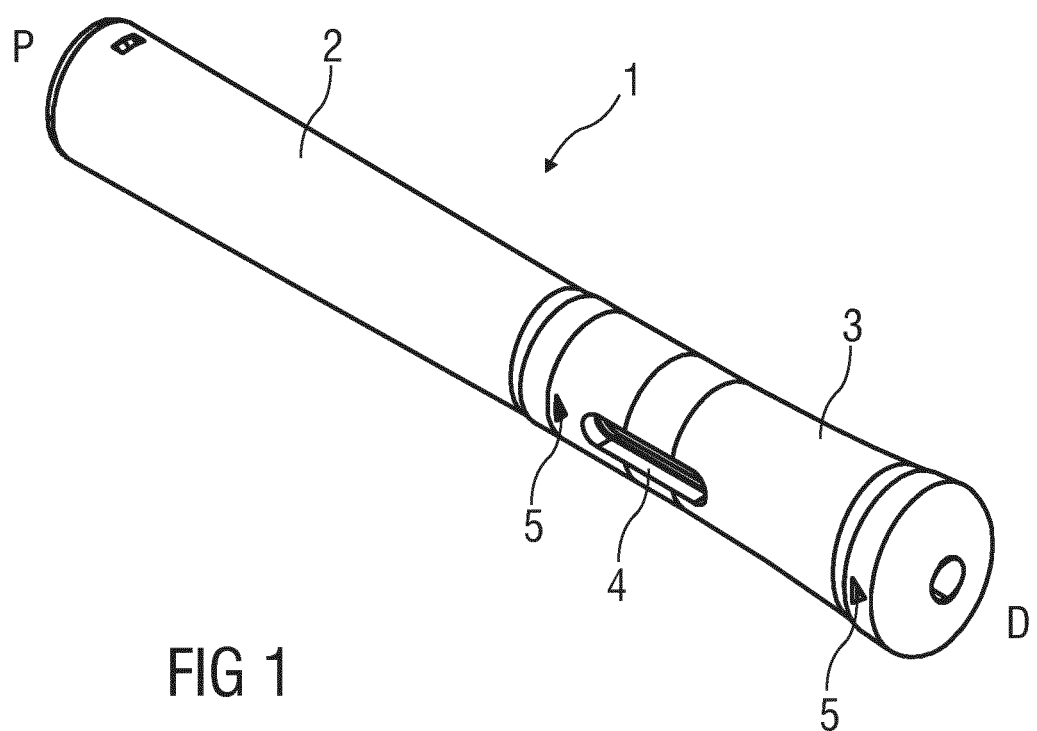
FIG. 1 is a perspective view of an exemplary embodiment of a medicament delivery device according to the present invention.

FIG. 1 is a perspective view of an exemplary embodiment of a medicament delivery device 1 according to the present invention. The medicament delivery device 1 comprises a body 2 which may be generally cylindrical. In an exemplary embodiment, a cap 3 may be removably coupled to the body 2. The cap 3 may include a viewing window 4 (e.g., an opening or a substantially transparent piece of material). The cap 3 may further include one or more indicia 5 for providing a visual and/or tactile indication of use (e.g., which end of the device 1 should be applied to an injection site, etc.). For example, in an exemplary embodiment, the indicia 5 include one or more arrows (painted or embossed) pointing toward a distal end of the device 1.

Figure 2A:
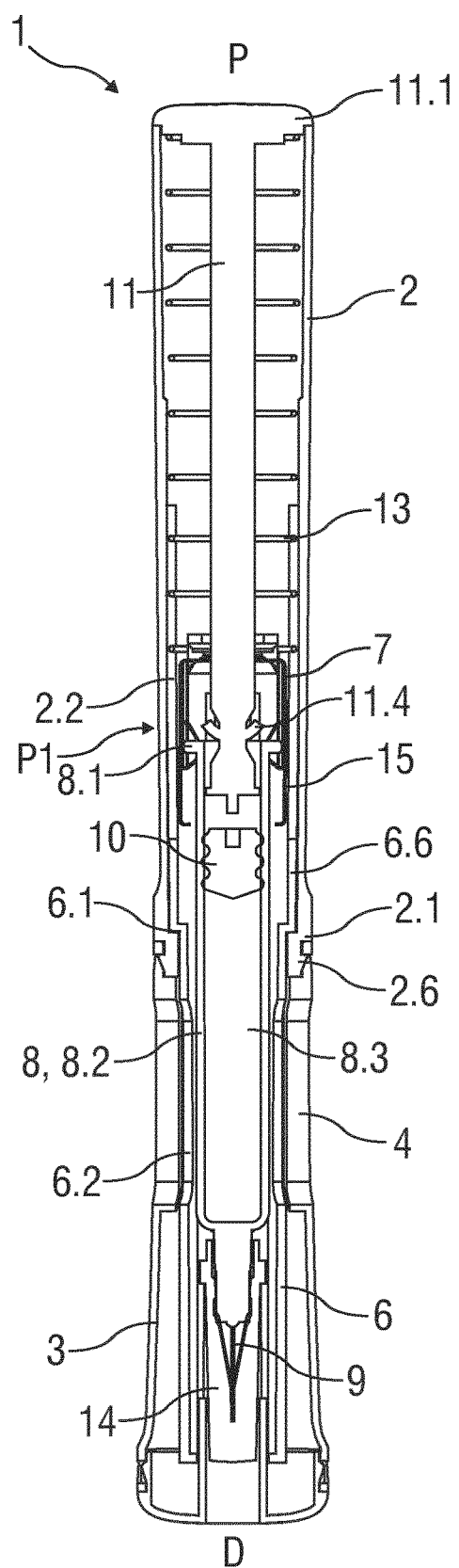
FIG. 2A is a schematic longitudinal section of an exemplary embodiment of a medicament delivery device according to the present invention prior to use.
Figure 2B:
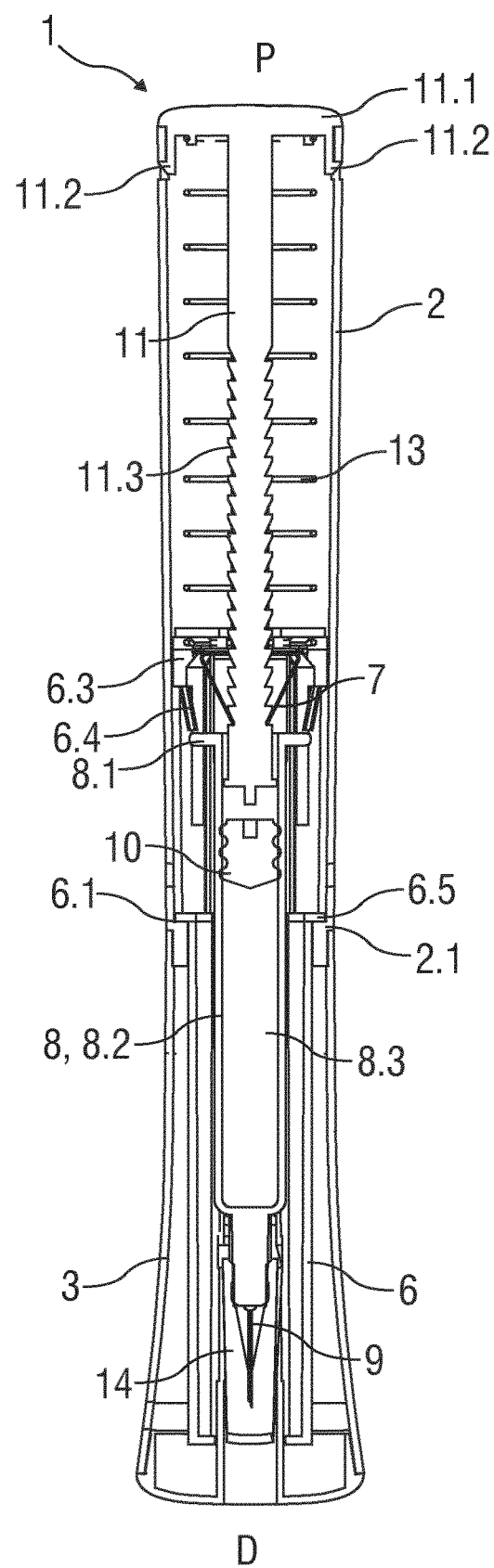
FIG. 2B is a schematic longitudinal section of an exemplary embodiment of a medicament delivery device according to the present invention prior to use.

FIGS. 2A and 2B show a longitudinal section of an exemplary embodiment of a medicament delivery device 1 according to the present invention. A sleeve 6 is slidably coupled to the body 2. For example, the sleeve 6 may be telescoped within the body 2. In an exemplary embodiment, the sleeve 6 comprises one or more lateral sleeve windows 6.2 adapted to axially align with the viewing windows 4 (e.g., an opening or a substantially transparent piece of material) in the cap 3 when the sleeve 6 is in an extended position (as shown in FIG. 2) relative to the body 2.

In an exemplary embodiment, a container carrier 7 slidably disposed in the body 2. The container carrier 7 is adapted to retain a medicament container, e.g., a syringe 8, an ampoule, a cartridge, etc. For example, the syringe 8 includes a syringe barrel 8.2 arranged as a hollow cylinder defining a cavity 8.3 for receiving a medicament. A needle 9 is arranged at a distal end of the syringe barrel 8.2 in a manner to be in fluid communication with the cavity 8.3. A stopper 10 is disposed within the syringe barrel 8.2 for proximally limiting the cavity 8.3. The stopper 10 may be displaced within the syringe barrel 8.2 for ejecting the medicament from the cavity 8.3 through the needle 9.

Figure 3:
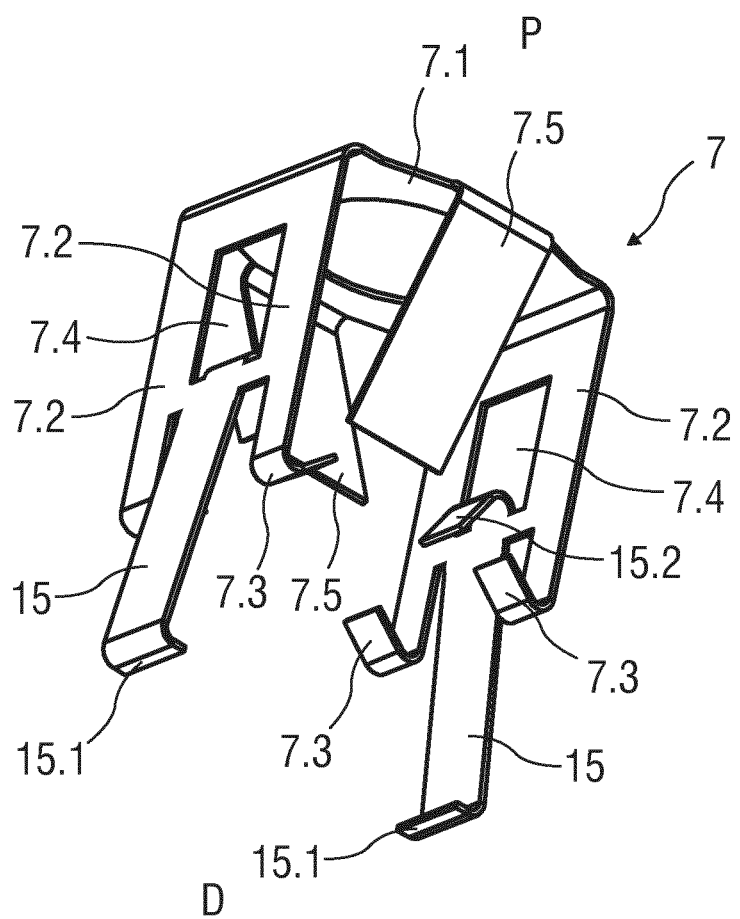
FIG. 3 is a schematic perspective view of an exemplary embodiment of a container carrier according to the present invention.

FIG. 3 shows an exemplary embodiment of a container carrier 7 according to the present invention. The container carrier 7 comprises a proximal portion 7.1 One or more first legs 7.2 extend distally from the proximal portion 7.1. In an exemplary embodiment, the first leg 7.2 comprises a radially inwardly directed first protrusion 7.3 arranged on a distal end of the first leg 7.2 and an aperture 7.4 (or recess). One or more second legs 7.5 extend distally from the proximal portion 7.1. The second leg 7.5 is biased radially inward.

In an exemplary embodiment, the container carrier 7 comprises one or more clamps 15 with a distal hook 15.1 and a proximal hook 15.2, wherein the proximal hook 15.2 is adapted to proximally engage a medicament container.

Referring again to FIGS. 2A and 2B, the body 2 comprises one or more longitudinal first ribs 2.2 having a first axial length and adapted to radially outwardly abut the clamps 15 when the carrier 7 is in a first position P1 relative to the body 2, as shown in FIGS. 2A and 2B. When the carrier 7 is moved from the first position P1 in the proximal direction P the clamps 15 slide along the first ribs 2.2.

In an exemplary embodiment, the sleeve 6 comprises one or more sleeve legs 6.6 extending in the proximal direction P beyond a collar 6.1. The sleeve legs 6.6 are adapted to radially outwardly support the clamps 15 such that they cannot deflect radially outwards depending on the axial position of the sleeve 6 relative to the clamps 15. The sleeve 6 comprises a proximal stop 6.4 and a distal stop 6.5. The proximal stop 6.4 is adapted to engage the sleeve 6 for limiting axial movement of the sleeve 6 in the distal direction D. In an exemplary embodiment the distal stop 6.5 may be part of the collar 6.1.

In an exemplary embodiment, a piston rod 11 is arranged within the body 2 in a manner to engage the stopper 10 for displacing it within the syringe barrel 8.2. In an exemplary embodiment, the piston rod 11 is attached to the body 2, preventing relative movement between the piston rod 11 and the body 2. In an exemplary embodiment the piston rod 11 may be integrally shaped with the body 2, or in another exemplary embodiment, the piston rod 11 may be secured to the body 2 by latches 11.2. In an exemplary embodiment, prior to use, an axial gap may be present between a distal end of the piston rod 11 and a proximal end of the stopper 10. The axial gap may prevent force being applied to the stopper 10 prior to use.

In an exemplary embodiment, a spring 13 is arranged over the piston rod 11 between a proximal end face 11.1 of the piston rod 11 and a spring seat 6.3 on the sleeve 6 thus biasing the sleeve 6 in the distal direction D relative to the piston rod 11 and body 2.

In an exemplary embodiment, the piston rod 11 comprises a ratchet toothing 11.3 adapted to be engaged by the second legs 7.5 of the carrier 7 in such a manner that the carrier 7 can move in the proximal direction P but is prevented from moving in the distal direction D relative to the piston rod 11.

In an exemplary embodiment, a syringe retarder 11.4 is provided on the piston rod 11. The syringe retarder 11.4 comprises one or more resilient arms which in a relaxed state define a diameter greater than an internal diameter of the syringe barrel 8.2. In the initial state shown in FIG. 4 the syringe retarder 11.4 abuts the proximal end of the syringe barrel 8.2 such that the syringe 8 cannot move in the proximal direction P relative to the piston rod 11. On application of a predefined force to the syringe 8 in the proximal direction P relative to the piston rod 11, the resilient arms may be deflected radially inward, such that the piston rod 11 can enter the syringe barrel 8.2 thus allowing movement of the piston rod 11 relative to the syringe 8 in the distal direction D.

In an exemplary embodiment, a protective needle shield 14 is arranged over the needle 9. The cap 3 is adapted to engage the needle shield 14, e.g. by a barb, in manner to remove it from the needle as the cap 3 is removed from the body 2 by pulling it in the distal direction D. A snap feature 2.6 may be arranged on the body 2 for releasably snap fitting the cap 3 to the body 2.

In order to perform an injection, the medicament delivery device 1 may be operated according to the following exemplary method.

The cap 3 is pulled in the distal direction D relative to the body 2 thereby also pulling the protective needle shield 14 off the needle 9. The syringe 8 is prevented from moving in the distal direction D as its proximal flange 8.1 abuts the first protrusion 7.3 of the carrier 7 being in the first position P1. The carrier 7 is prevented from moving in the distal direction D by the second legs 7.5 being engaged to the ratchet 11.3. The collar 6.1 on the sleeve 6 distally abuts an axial stop 2.1 on the body 2 such that the sleeve 6 is also prevented from moving in the distal direction D.

Figure 4:
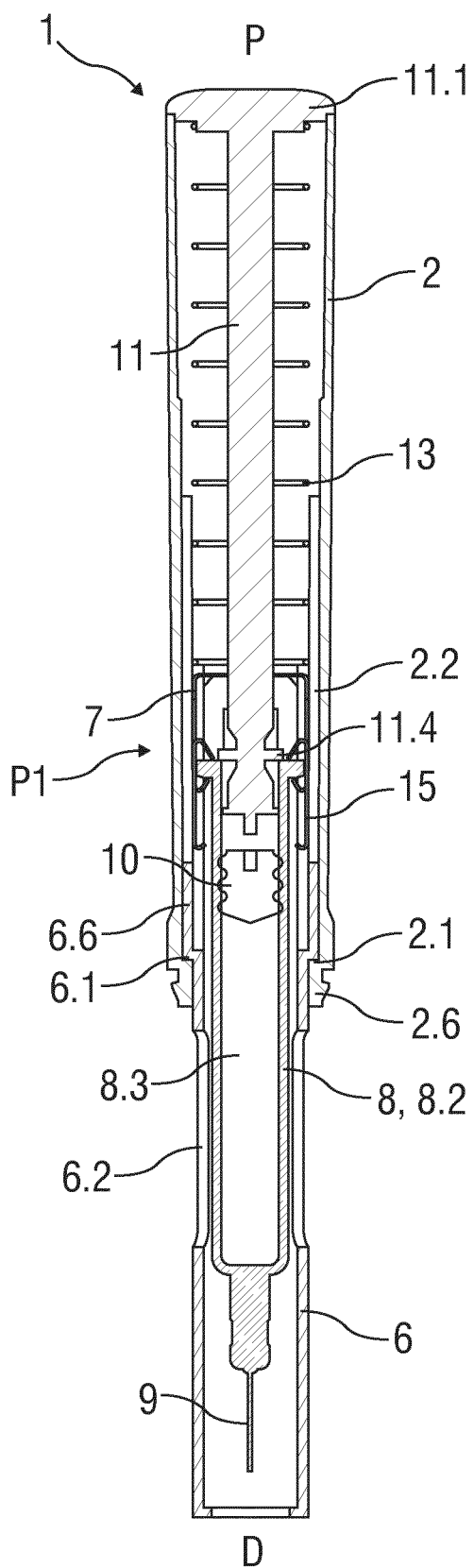
FIG. 4 is a schematic longitudinal section of an exemplary embodiment of a medicament delivery device according to the present invention prior to use.

FIG. 4 is a schematic longitudinal section of the medicament delivery device 1 after removal of the cap 3 and the protective needle shield 14. The needle 9 is located within the sleeve 6 preventing a user from touching and seeing it. In this state the medicament delivery device 1 may be held at the body 2 and the sleeve 6 may be pushed against an injection site, e.g. a patient's skin. Consequently the sleeve 6 moves in the proximal direction P relative to the body 2 against the force of the spring 13, as the spring 13 is applying a biasing force on the spring seat 6.3 of the sleeve 6. Due to the movement of the sleeve 6 in the proximal direction P, the spring 13 is compressed. The syringe 8 remains in position relative to the body 2 due to the syringe retarder 11.4. As the syringe 8 and the needle 9 stay in position relative to the body 2 while the sleeve 6 moves in the proximal direction P, the needle 9 protrudes beyond a distal end of the sleeve 6 and is inserted into the injection site. Once the distal stop 6.5 abuts the flange 8.1 on the syringe 8, movement of the sleeve 6 relative to the syringe 8 and needle 9 stops. The needle 9 has reached its insertion depth. Any further movement of the sleeve 6 relative to the body 2 in the proximal direction P hence causes deformation of the syringe retarder 11.4, and the container carrier 7 moves proximally out of the first position P1 relative to the body 2.

Figure 5A:
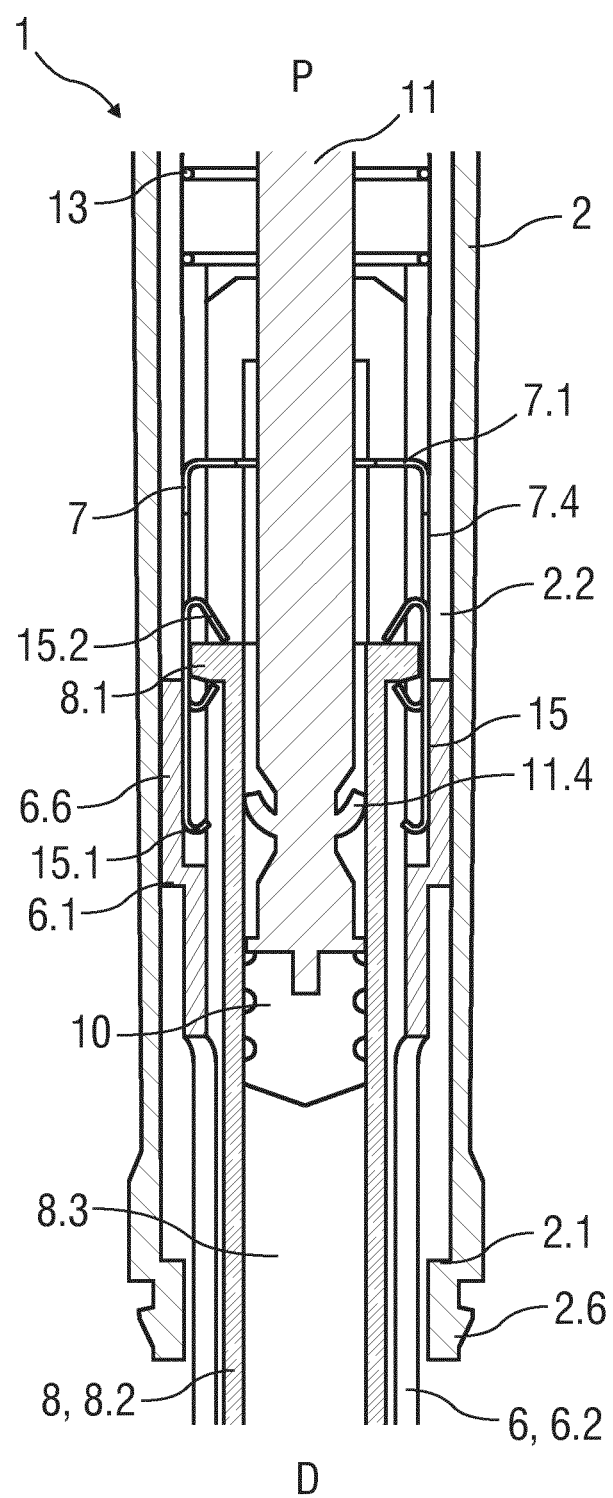
FIG. 5A is a schematic longitudinal detail section of an exemplary embodiment of a medicament delivery device according to the present invention during use.
Figure 5B:
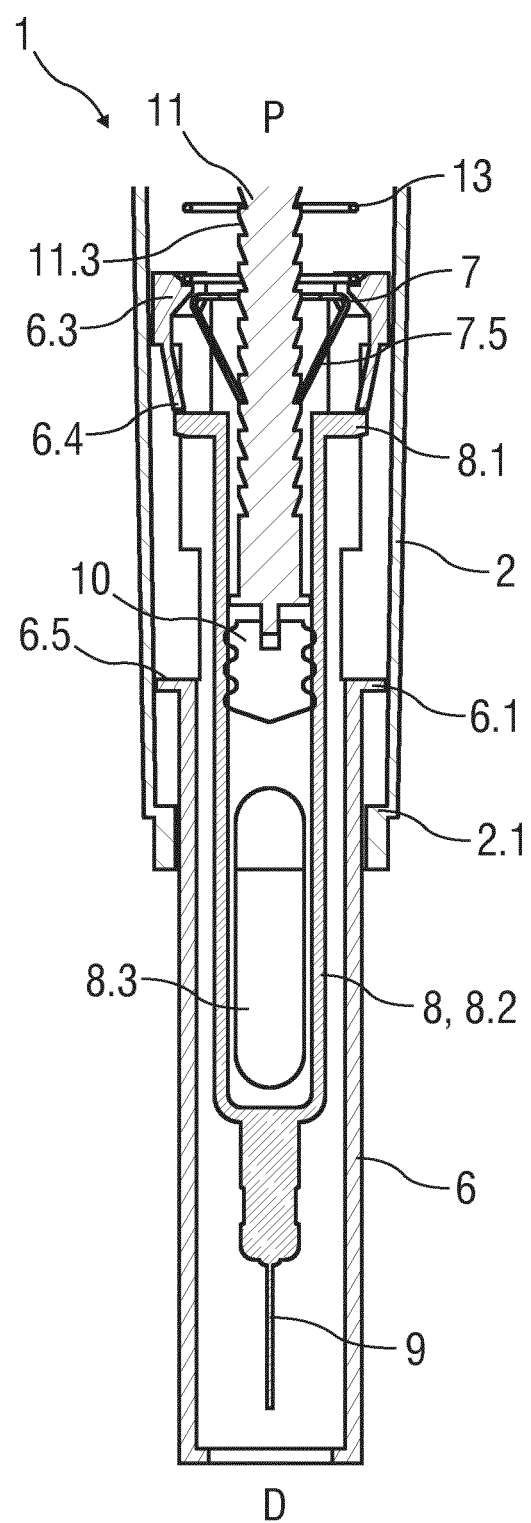
FIG. 5B is a schematic longitudinal detail section of an exemplary embodiment of a medicament delivery device according to the present invention during use.

FIGS. 5A and 5B are schematic longitudinal detail sections in different section planes of the medicament delivery device 1 with the syringe 8 having moved in the proximal direction P relative to the piston rod 11. The increase in force required to deform the syringe retarder 11.4 may be a tactile feedback experienced by a user. As the piston rod 11 is coupled to the body 2, movement of the syringe 8 in the proximal direction P causes the piston rod 11 to abut the stopper 10 and displace it within the syringe barrel 8.2 ejecting the drug from the cavity 8.3 through the needle 9 into the injection site. As the sleeve 6 keeps moving relative to the body 2 the spring 13 is further compressed thus increasing its force according to Hooke's law thus providing a tactile feedback to the user about the state of the injection. As the syringe 8 moves in the proximal direction P relative to the body 2 and the piston rod 11, the flange 8.1 engages the proximal hook 15.2 within the carrier 7. Hence, the carrier 7 is also moved in the proximal direction P relative to the piston rod 11 thereby causing the second legs 7.5 to move along the ratchet toothing 11.3. As the second legs 7.5 disengage and engage successive teeth in the ratchet, an audible feedback may be provided in the form of a "click" sound.

If the medicament delivery device 1 was removed from the injection site use, the spring 13 would return the sleeve 6 in the distal direction D as in FIG. 5B until the proximal stop 6.4 of the sleeve 6 abuts the flange 8.1. As the second legs 7.5 of the carrier 7 are engaged in the ratchet toothing 11.3 the carrier 7, the syringe 8 and the needle 9 are prevented from returning in the distal direction D. The needle 9 would be hence covered again by the sleeve 6 despite the changed axial position of the syringe 8 relative to the body 2.

Figure 6:
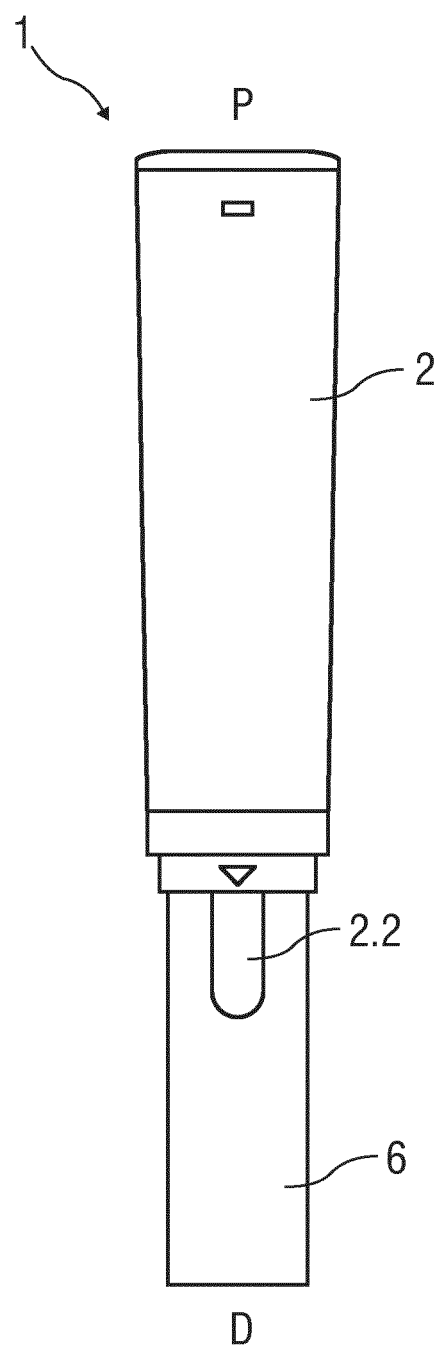
FIG. 6 is a schematic view of an exemplary embodiment of a medicament delivery device according to the present invention during interruption of delivery.

FIG. 6 is a schematic view of the medicament delivery device 1 having been removed from the injection site after partial delivery of the medicament. The overall length of the medicament delivery device 1 is shorter than in the initial state and the sleeve windows 6.2 are partially hidden within the body 2 thus providing a visual feedback as to the progress of the injection and as to the state of use of the device 1.

If the medicament delivery device 1 is in this state it can be re-applied against the injection site and the injection can be continued. The sleeve 6 will again move relative to the syringe 8 thus inserting the needle 9 into the injection site before the sleeve 6 abuts the syringe 8 moving it relative to the body 2 and piston rod 11 for delivering the drug thereby also moving the camps 15 and the carrier 7.

Figure 7:
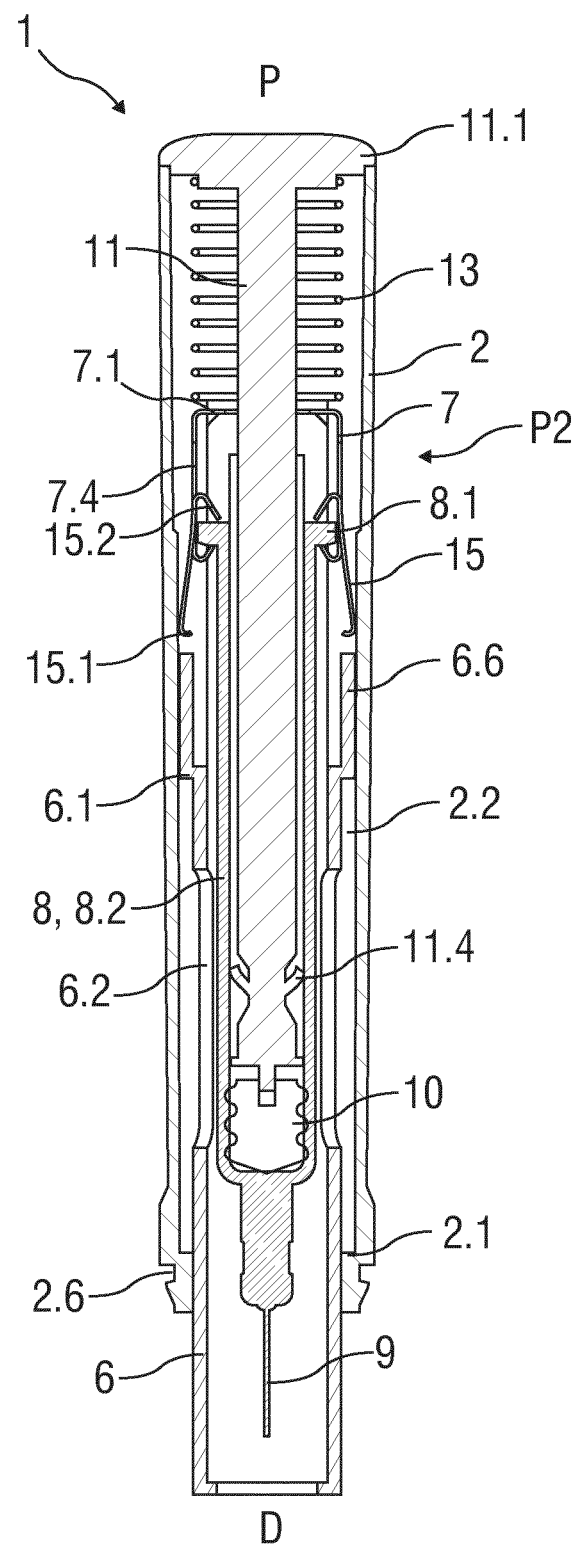
FIG. 7 is a schematic longitudinal section of an exemplary embodiment of a medicament delivery device according to the present invention after use.
Figure 8:
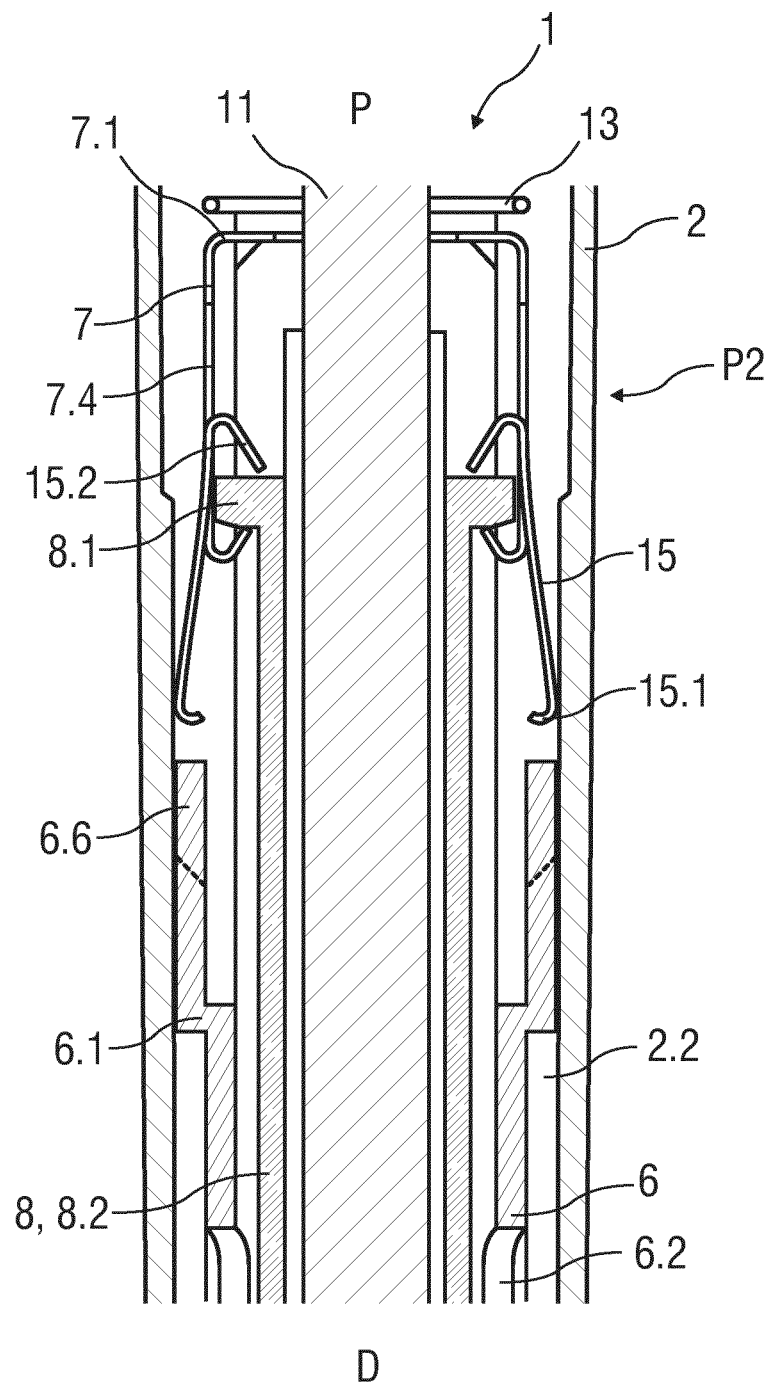
FIG. 8 is a schematic longitudinal detail section of an exemplary embodiment of a medicament delivery device according to the present invention after use.

If after the initial start or after restart of the injection the body 2 is at least nearly fully depressed relative to the sleeve 6, the piston rod 11 will displace the stopper 10 until the stopper 10 bottoms out within the syringe 8 thereby at least nearly fully emptying the cavity 8.3. At this point the force opposing the movement of the body 2 in the distal direction D relative to the sleeve 6 considerably increases indicating to the user that the injection is finished. At this point the container carrier 7 has traveled to or beyond a second position P2 such that the clamps 15 could deflect radially outwards. However, as long as the sleeve 6 is maintained depressed the sleeve legs 6.6 still outwardly support the clamps 15 preventing their outward deflection. FIG. 7 is a schematic longitudinal section of the medicament delivery device 1 with the carrier 7 in the second position P2. FIG. 8 is a schematic longitudinal detail section of the medicament delivery device 1 with the carrier 7 in the second position P2, wherein the sleeve 6 is shown transparently to allow seeing the rib 2.2.

When the medicament delivery device 1 is been removed from the injection site, the spring 13 returns the sleeve 6 in the distal direction D relative to the carrier 7, syringe 8 and needle 9 until the proximal stop 6.4 on the sleeve 6 abuts the flange 8.1 of the syringe 8 thereby axially removing the sleeve legs 6.6 from the clamps 15 allowing them to radially outwardly deflect. Due to the movement of the sleeve 6 relative to the carrier 7, the needle 9 is covered again by the sleeve 6. On an attempt to again move the sleeve 6 in the proximal direction P relative to the body 2, the sleeve legs 6.6 would axially abut the outwardly deflected clamps 15 preventing re-exposure of the needle 9. The length of the first rib 2.2 can be modified in order to adapt the position and hence the percentage of drug delivered at which the clamps 15 are allowed to deflect radially outwards and lock out the sleeve 6.

The cap 3 of the medicament delivery device 1 serves for keeping the needle sterile prior to use, for removing the protective needle shield 14, for preventing unintended use of the medicament delivery device 1 prior to removal of the cap 3 and for providing rigid packaging.

The medicament delivery device 1 allows for application by a user, e.g. a patient or caregiver, wherein the body 2 can be held in one hand. The needle 9 of the medicament delivery device 1 is hidden from view during all states of operation.

The forces required to insert the needle 9 into the injection site and to deliver the drug can be adjusted by respectively selecting the spring 13, wherein the force for delivering the drug depends on the spring 13 and on the characteristics of the syringe 8, stopper 10, needle 9 and drug as well as on the friction between the syringe retarder 11.4 on the inner wall of the syringe barrel 8.2.

The function of the ribs 2.2 could likewise be provided by a step in the inner surface of the body 2.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, -continued H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device, comprising:
a body,
a container carrier for retaining a medicament container within the body, the container carrier slidably disposed in the body,
a sleeve slidably coupled to body, and
a piston rod coupled to the body and the container carrier, wherein the piston rod and the container carrier are configured to provide a feedback as the container carrier moves from a first position to a second position relative to the body, wherein the container carrier comprises one or more radially inwardly biased legs adapted to engage a ratchet toothing on the piston rod in such a manner that the container carrier can move in a proximal direction but is prevented from moving in a distal direction relative to the piston rod, and wherein the sleeve comprises a proximal stop and a distal stop adapted to abut the medicament container.

2. The medicament delivery device according to claim 1, wherein the piston rod is coupled to the body in a manner preventing relative movement between the piston rod and the body.

3. The medicament delivery device according to claim 1, further comprising a spring arranged between the body and the sleeve and biasing the sleeve in a distal direction relative to the body.

4. The medicament delivery device according to claim 1, wherein the sleeve comprises one or more sleeve windows.

5. The medicament delivery device according to claim 1, wherein the container carrier comprises at least one first protrusion adapted to distally abut the medicament container.

6. The medicament delivery device according to claim 1, further comprising at least one clamp arranged on the container carrier and adapted to proximally abut the medicament container.

7. The medicament delivery device according to claim 6, wherein the body includes a rib configured to radially abut the clamp to maintain the clamp in a first angular position when the container carrier is in the first position, and wherein the clamp is configured to deflect radially to a second angular position when the container carrier is in the second position.

8. The medicament delivery device according to claim 7, wherein the clamp is adapted to axially abut the sleeve in the second angular position when the container carrier is in the second position.

9. The medicament delivery device according to claim 7, wherein the sleeve comprises one or more sleeve legs extending in the proximal direction adapted to radially outwardly support the clamp.

10. The medicament delivery device according to claim 1, wherein the piston rod includes a deformable syringe retarder having a diameter greater than an internal diameter of the medicament container, wherein the deformable syringe retarder is configured to deform on application of a predefined force on the medicament container in the proximal direction relative to the piston rod.

11. The medicament delivery device according to claim 7, wherein the clamp comprises a proximal hook adapted to proximally engage the medicament container.

12. The medicament delivery device according to claim 1, wherein the sleeve comprises a collar adapted to distally abut an axial stop on the body.

13. The medicament delivery device according to claim 1, wherein a cap is configured to be arranged over a distal end of the body, and wherein the cap is adapted to engage a protective needle shield.

14. The medicament delivery device of claim 1, wherein the container carrier retains the medicament container within the body and wherein the medicament container holds a pharmaceutically active compound.

15. A medicament delivery device, comprising:
a body,
a container carrier for retaining a medicament container within the body, the container carrier slidably disposed in the body,
a sleeve slidably coupled to body, and
a piston rod coupled to the body and the container carrier, wherein the piston rod and the container carrier are configured to provide a feedback as the container carrier moves from a first position to a second position relative to the body, wherein the container carrier comprises one or more radially inwardly biased legs adapted to engage a ratchet toothing on the piston rod in such a manner that the container carrier can move in a proximal direction but is prevented from moving in a distal direction relative to the piston rod,
wherein the container carrier comprises at least one first protrusion adapted to distally abut the medicament container.

16. The medicament delivery device according to claim 15, wherein the piston rod is coupled to the body in a manner preventing relative movement between the piston rod and the body.

17. The medicament delivery device of claim 15, wherein the container carrier retains the medicament container within the body and wherein the medicament container holds a pharmaceutically active compound.

18. A medicament delivery device, comprising:
a body,
a container carrier for retaining a medicament container within the body, the container carrier slidably disposed in the body,
a sleeve slidably coupled to body,
a piston rod coupled to the body and the container carrier, and
at least one clamp arranged on the container carrier and adapted to proximally abut the medicament container,
wherein the piston rod and the container carrier are configured to provide a feedback as the container carrier moves from a first position to a second position relative to the body, wherein the container carrier comprises one or more radially inwardly biased legs adapted to engage a ratchet toothing on the piston rod in such a manner that the container carrier can move in a proximal direction but is prevented from moving in a distal direction relative to the piston rod.

19. The medicament delivery device according to claim 18, wherein the body includes a rib configured to radially abut the clamp to maintain the clamp in a first angular position when the container carrier is in the first position, and wherein the clamp is configured to deflect radially to a second angular position when the container carrier is in the second position.

20. The medicament delivery device of claim 18, wherein the container carrier retains the medicament container within the body and wherein the medicament container holds a pharmaceutically active compound.

* * * * *

SEQUENCE LISTING

```
<160> NUMBER OF SEQ ID NOS: 40

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 41
<212> TYPE: PRT
<213> ORGANISM: Artificial Sequence
<220> FEATURE:
<223> OTHER INFORMATION: H-(Lys)4-des Pro36, des Pro37 Exendin-4(1-39)-
      NH2

<400> SEQUENCE: 2

Lys Lys Lys Lys His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Ser
        35                  40

<210> SEQ ID NO 3
<211> LENGTH: 42
<212> TYPE: PRT
<213> ORGANISM: Artificial Sequence
<220> FEATURE:
<223> OTHER INFORMATION: H-(Lys)5-des Pro36, des Pro37 Exendin-4(1-39)-
      NH2

<400> SEQUENCE: 3

Lys Lys Lys Lys Lys His Gly Glu Gly Thr Phe Thr Ser Asp Leu Ser
1               5                   10                  15

Lys Gln Met Glu Glu Glu Ala Val Arg Leu Phe Ile Glu Trp Leu Lys
            20                  25                  30

Asn Gly Gly Pro Ser Ser Gly Ala Pro Ser
        35                  40

<210> SEQ ID NO 4
<211> LENGTH: 38
<212> TYPE: PRT
<213> ORGANISM: Artificial Sequence
<220> FEATURE:
<223> OTHER INFORMATION: des Pro36 Exendin-4(1-39)
```

```
<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 38
<212> TYPE: PRT
<213> ORGANISM: Artificial Sequence
<220> FEATURE:
<223> OTHER INFORMATION: des Pro36 [Asp28] Exendin-4(1-39)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: des Pro36 [IsoAsp28] Exendin-4(1-39)
<220> FEATURE:
<221> NAME/KEY: MISC_FEATURE
<222> LOCATION: (28)..(28)
<223> OTHER INFORMATION: x=isoaspartate

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Pro Ser
        35

<210> SEQ ID NO 7
<211> LENGTH: 38
<212> TYPE: PRT
<213> ORGANISM: Artificial Sequence
<220> FEATURE:
<223> OTHER INFORMATION: des Pro36 [Met(O)14, Asp28] Exendin-4(1-39)
<220> FEATURE:
<221> NAME/KEY: MISC_FEATURE
<222> LOCATION: (14)..(14)
<223> OTHER INFORMATION: x=methionine oxide

<400> SEQUENCE: 7

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35
```

```
<210> SEQ ID NO 8
<211> LENGTH: 38
<212> TYPE: PRT
<213> ORGANISM: Artificial Sequence
<220> FEATURE:
<223> OTHER INFORMATION: des Pro36 [Met(O)14, IsoAsp28] Exendin-4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (28)..(28)
<223> OTHER INFORMATION: x=isoaspartate

<400> SEQUENCE: 8

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 9
<211> LENGTH: 38
<212> TYPE: PRT
<213> ORGANISM: Artificial Sequence
<220> FEATURE:
<223> OTHER INFORMATION: des Pro36 [Trp(O2)25, Asp28] Exendin-4(1-39)
<220> FEATURE:
<221> NAME/KEY: MISC_FEATURE
<222> LOCATION: (25)..(25)
<223> OTHER INFORMATION: x=tryptophan dioxide

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Artificial Sequence
<220> FEATURE:
<223> OTHER INFORMATION: des Pro36 [Trp(O2)25, IsoAsp28] Exendin-4(1-39)
<220> FEATURE:
<221> NAME/KEY: MISC_FEATURE
<222> LOCATION: (25)..(25)
<223> OTHER INFORMATION: x=tryptophan dioxide
<220> FEATURE:
<221> NAME/KEY: MISC_FEATURE
<222> LOCATION: (28)..(28)
<223> OTHER INFORMATION: x=isoaspartate

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35
```

-continued

```
<210> SEQ ID NO 11
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, Asp28] Exendin-
      4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan dioxide

<400> SEQUENCE: 11

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 12
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, IsoAsp28]
      Exendin-4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan dioxide
<220> FEATURE:
<221> NAME/KEY: MISC_FEATURE
<222> LOCATION: (28)..(28)
<223> OTHER INFORMATION: x=isoapartate

<400> SEQUENCE: 12

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 13
<211> LENGTH: 44
<212> TYPE: PRT
<213> ORGANISM: Artificial Sequence
<220> FEATURE:
<223> OTHER INFORMATION: des Pro36 Exendin-4(1-39)-Lys6-NH2

<400> SEQUENCE: 13

His Gly Glu Gly Thr Lys Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```

<210> SEQ ID NO 14
<211> LENGTH: 50
<212> TYPE: PRT
<213> ORGANISM: Artificial Sequence
<220> FEATURE:
<223> OTHER INFORMATION: H-(Lys)6-des Pro36 [Asp28] Exendin-4(1-39)-
      Lys6-NH2

<400> SEQUENCE: 14

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 15
<211> LENGTH: 38
<212> TYPE: PRT
<213> ORGANISM: Artificial Sequence
<220> FEATURE:
<223> OTHER INFORMATION: des Asp28 Pro36, Pro37, Pro38Exendin-4(1-39)-
      NH2

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
            20                  25                  30

Gly Ala Pro Pro Pro Ser
        35

<210> SEQ ID NO 16
<211> LENGTH: 44
<212> TYPE: PRT
<213> ORGANISM: Artificial Sequence
<220> FEATURE:
<223> OTHER INFORMATION: H-(Lys)6-des Pro36, Pro38 [Asp28] Exendin-4(1-
      39)-NH2

<400> SEQUENCE: 16

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 17
<211> LENGTH: 44
<212> TYPE: PRT
<213> ORGANISM: Artificial Sequence
<220> FEATURE:
<223> OTHER INFORMATION: H-Asn-(Glu)5des Pro36, Pro37, Pro38 [Asp28]
      Exendin-4(1-39)-NH2

```
<400> SEQUENCE: 17

Asn Glu Glu Glu Glu Glu His Gly Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40

<210> SEQ ID NO 18
<211> LENGTH: 44
<212> TYPE: PRT
<213> ORGANISM: Artificial Sequence
<220> FEATURE:
<223> OTHER INFORMATION: des Pro36, Pro37, Pro38 [Asp28] Exendin-4(1-
      39)-(Lys)6-NH2

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 19
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Asp28]
      Exendin-4(1-39)-(Lys)6-NH2

<400> SEQUENCE: 19

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 20
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Asp28]
      Exendin-4(1-39)-(Lys)6-NH2

<400> SEQUENCE: 20

Asn Glu Glu Glu Glu Glu His Gly Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys
        35                  40                  45

Lys Lys
    50
```

```
<210> SEQ ID NO 21
<211> LENGTH: 50
<212> TYPE: PRT
<213> ORGANISM: Artificial Sequence
<220> FEATURE:
<223> OTHER INFORMATION: H-(Lys)6-des Pro36 [Trp(O2)25, Asp28] Exendin-
      4(1-39)-Lys6-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 21

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 22
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Trp(O2)25]
      Exendin-4(1-39)-NH2
<220> FEATURE:
<221> NAME/KEY: MISC_FEATURE
<222> LOCATION: (25)..(25)
<223> OTHER INFORMATION: x=tryptophan dioxide

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Gly Gly Pro Ser Ser
            20                  25                  30

Gly Ala Pro Pro Pro Ser
        35

<210> SEQ ID NO 23
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 23

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 24
<211> LENGTH: 44
<212> TYPE: PRT
<213> ORGANISM: Artificial Sequence
```

<220> FEATURE:
<223> OTHER INFORMATION: H-Asn-(Glu)5-des Pro36, Pro37, Pro38
    [Trp(O2)25, Asp28] Exendin-4(1-39)-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 24

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 25
<211> LENGTH: 44
<212> TYPE: PRT
<213> ORGANISM: Artificial Sequence
<220> FEATURE:
<223> OTHER INFORMATION: des Pro36, Pro37, Pro38 [Trp(O2)25, Asp28]
    Exendin-4(1-39)-(Lys)6-NH2
<220> FEATURE:
<221> NAME/KEY: MISC_FEATURE
<222> LOCATION: (25)..(25)
<223> OTHER INFORMATION: x=tryptophan dioxide

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 26
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
    Asp28] Exendin-4(1-39)-(Lys)6-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 26

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 27
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38
    [Trp(O2)25, Asp28] Exendin-4(1-39)-(Lys)6-NH2

```
<220> FEATURE:
<221> NAME/KEY: MISC_FEATURE
<222> LOCATION: (31)..(31)
<223> OTHER INFORMATION: x=tryptophan dioxide

<400> SEQUENCE: 27

Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys
        35                  40                  45

Lys Lys
    50

<210> SEQ ID NO 28
<211> LENGTH: 50
<212> TYPE: PRT
<213> ORGANISM: Artificial Sequence
<220> FEATURE:
<223> OTHER INFORMATION: H-(Lys)6-des Pro36 [Met(O)14, Asp28] Exendin-
      4(1-39)-Lys6-NH2
<220> FEATURE:
<221> NAME/KEY: MISC_FEATURE
<222> LOCATION: (20)..(20)
<223> OTHER INFORMATION: x=methionine oxide

<400> SEQUENCE: 28

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 29
<211> LENGTH: 38
<212> TYPE: PRT
<213> ORGANISM: Artificial Sequence
<220> FEATURE:
<223> OTHER INFORMATION: des Met(O)14 Asp28 Pro36, Pro37, Pro38 Exendin-
      4(1-39)-NH2

<400> SEQUENCE: 29

His Gly Glu Gly Thr Phe Thr Ser Asp Leu Ser Lys Gln Glu Glu Glu
1               5                   10                  15

Ala Val Arg Leu Phe Ile Glu Trp Leu Lys Asp Gly Gly Pro Ser Ser
            20                  25                  30

Gly Ala Pro Pro Pro Ser
        35

<210> SEQ ID NO 30
<211> LENGTH: 44
<212> TYPE: PRT
<213> ORGANISM: Artificial Sequence
<220> FEATURE:
<223> OTHER INFORMATION: H-(Lys)6-desPro36, Pro37, Pro38 [Met(O)14,
      Asp28] Exendin-4(1-39)-NH2
<220> FEATURE:
<221> NAME/KEY: MISC_FEATURE
<222> LOCATION: (20)..(20)
<223> OTHER INFORMATION: x=methionine oxide
```

<400> SEQUENCE: 30

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
            35                  40

<210> SEQ ID NO 31
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Asp28] Exendin-4(1-39)-NH2
<220> FEATURE:
<221> NAME/KEY: MISC_FEATURE
<222> LOCATION: (20)..(20)
<223> OTHER INFORMATION: x=methionine oxide

<400> SEQUENCE: 31

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
            35                  40

<210> SEQ ID NO 32
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Asp28]
      Exendin-4(1-39)-(Lys)6-NH2
<220> FEATURE:
<221> NAME/KEY: MISC_FEATURE
<222> LOCATION: (14)..(14)
<223> OTHER INFORMATION: x=methionine oxide

<400> SEQUENCE: 32

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 33
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide

<400> SEQUENCE: 33

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

<210> SEQ ID NO 34
<211> LENGTH: 50
<212> TYPE: PRT
<213> ORGANISM: Artificial Sequence
<220> FEATURE:
<223> OTHER INFORMATION: H-Asn-(Glu)5 des Pro36, Pro37, Pro38 [Met(O)14, Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide

<400> SEQUENCE: 34

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 35
<211> LENGTH: 50
<212> TYPE: PRT
<213> ORGANISM: Artificial Sequence
<220> FEATURE:
<223> OTHER INFORMATION: H-Lys6-des Pro36 [Met(O)14, Trp(O2)25, Asp28] Exendin-4(1-39)-Lys6-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan dioxide

<400> SEQUENCE: 35

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 36
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Met(O)14, Trp(O2)25] Exendin-4(1-39)-NH2
<220> FEATURE:
<221> NAME/KEY: MISC_FEATURE
<222> LOCATION: (14)..(14)
<223> OTHER INFORMATION: x=methionine oxide

```
<220> FEATURE:
<221> NAME/KEY: MISC_FEATURE
<222> LOCATION: (25)..(25)
<223> OTHER INFORMATION: x=tryptophan oxide

<400> SEQUENCE: 36

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Gly Gly Pro Ser Ser
            20                  25                  30

Gly Ala Pro Pro Pro Ser
        35

<210> SEQ ID NO 37
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan oxide

<400> SEQUENCE: 37

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 38
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Trp(O2)25,
      Asp28] Exendin-4(1-39)-(Lys)6-NH2
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan oxide

<400> SEQUENCE: 38

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 39
<211> LENGTH: 50
<212> TYPE: PRT
<213> ORGANISM: Artificial Sequence
```

```
<220> FEATURE:
<223> OTHER INFORMATION: H-(Lys)6-des Pro36, Pro37, Pro38 [Met(O)14,
      Trp(O2)25, Asp28] Exendin-4(S1-39)-(Lys)6-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan oxide

<400> SEQUENCE: 39

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 40
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan oxide

<400> SEQUENCE: 40

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50
```